US005131404A

United States Patent [19]

Neeley et al.

[11] Patent Number: 5,131,404

[45] Date of Patent: Jul. 21, 1992

[54] CAPILLARY TUBE CARRIER WITH PUTTY-FILLED CAP

[76] Inventors: William E. Neeley; Andrena C. Neeley, both of 22 High View Rd., both of Madison, Conn. 06443

[21] Appl. No.: 729,692

[22] Filed: Jul. 15, 1991

[51] Int. Cl.[5] ................ A61B 5/00

[52] U.S. Cl. ................ 128/763; 206/443

[58] Field of Search ................ 128/760, 763, 762, 764, 128/759; 73/863.31, 864.31, 864.02, 864.72, 864.82, 864.83, 864.86, 864.91; 206/443, 557, 564, 363, 364, 365, 366; 215/DIG. 3; 422/61, 100, 102, 104; 604/317, 256, 1

[56] References Cited

U.S. PATENT DOCUMENTS

| | | | |
|---|---|---|---|
| 3,612,321 | 10/1971 | Larson | 128/760 |
| 3,712,465 | 1/1973 | Deuschle | 206/443 |
| 3,811,326 | 5/1974 | Sokol | 128/760 |
| 4,122,947 | 10/1978 | Falla | 206/569 |
| 4,268,179 | 5/1981 | Long et al. | 400/120 |
| 4,576,595 | 3/1986 | Aas et al. | 604/256 |
| 4,738,827 | 4/1988 | Pierotti | 422/104 |
| 4,979,515 | 12/1990 | Briggs et al. | 128/760 |
| 4,981,144 | 1/1991 | Carels, Jr. | 128/760 |
| 5,018,621 | 5/1991 | O'Connell, Jr. | 206/204 |

*Primary Examiner*—Max Hindenburg
*Assistant Examiner*—Guy V. Tucker
*Attorney, Agent, or Firm*—William W. Jones

[57] ABSTRACT

Blood samples are drawn from patients in capillary tubes from skin sticks. When drawn, the capillary tubes for individual patients are placed in a single larger specimen carrier tube which can then be labeled with a specialized specimen label printed at bedside, or elsewhere, when the samples are drawn. The larger carrier tube has a closure cap which includes an internal layer of putty which is used to seal an end of the capillary tubes for each individual patient, thereby eliminating the possibility of cross contamination of one patient's blood sample with another's when the capillary tubes are plugged. The specimen tube also has an internal separator which will prevent the capillary tubes from touching each other to limit breakage of the capillary tubes during handling.

10 Claims, 2 Drawing Sheets

CAPILLARY TUBE CARRIER WITH PUTTY-FILLED CAP

FIELD OF THE INVENTION

This invention relates to procedures and paraphernalia for drawing, transporting, and labeling blood samples in capillary tubes. The procedures described herein can be used in conjunction with the subject matter disclosed in copending U.S. Ser. No. 07/410,144, filed Sep. 20, 1989 by W. E. Neeley and in U.S. Ser. No. 07/689,476, filed Apr. 23, 1991 by W. E. Neeley et al.

DESCRIPTION OF RELATED ART

Blood samples for analysis and specimen testing are presently taken from neo-natal (infant) and elderly patients with capillary tubes using skin sticks of the patients. Typically, the patients are stuck with the capillary tube in a finger, ear lobe, toe, or the like. So long as blood flows from the stick, specimens will be drawn into the capillary tubes. After the tubes fill with blood, one end of the tubes will be closed with a plug of putty formed by stabbing the tube into a slab of putty. Current procedures utilize a single slab of putty for use in closing all of the capillary tubes in a single blood drawing round. The use of a single putty slab to close all of the capillary tubes creates the possibility of contaminating one patient's blood sample with the blood from another patient. This possibility arises from the fact that residual blood will be left on the putty slab each time a capillary tube is plugged. If one patient's blood is contaminated with another patient's blood, the possibility of misleading or erroneous sample test results exists.

The different blood samples in each of the capillary tubes from each patient will be used to perform different specimen tests. For example, if four capillary tubes of blood are drawn from a single patient, then four different tests could be performed on the samples. A problem that exists with the drawing of several different blood samples from a single patient concerns labeling of the capillary tubes with proper specimen testing information so that the lab personnel will know what tests are to be performed on which specimen samples. The labels presently used for identifying patients and samples are large because they are sized to fit on VACUTAINER® or the like tubes, which are large evacuated tubes manufactured by Becton Dickinson and Company for drawing blood samples from adults. Such large labels are obviously not readily adaptable for use with capillary tubes. When affixed to a capillary tube, the information printed on the label may be obscured or obliterated. The labels can also become detached from the small capillary tubes in transport.

A third problem relating to the sampling of blood specimens in capillary tubes relates to the fragile nature of the tubes. The drawer will be taking many blood samples in the capillary tubes which tubes must then be transported back to the lab. Since the tubes are by their nature fragile, the possibility of capillary tube breakage after (or before) specimen sampling is a problem. If a tube breaks after sampling, the additional problem of contamination also exists. Presently, the capillary tubes are simply placed in the clay pad with the bottom of the capillary tubes being stuck in the clay pad. All of the blood samples are carried away from the sampling rounds in this manner. The blood capillary tubes are thus unprotected and are placed in a common carrier which is non-specific to patients, as rounds proceed.

From the above, it will be apparent that the use of capillary tubes for drawing blood samples creates a number of different problems that relate to blood sample security; to sample integrity, and to sample labeling.

Copending U.S. patent application Ser. No. 410,144, filed Sep. 20, 1989 by W. E. Neely discloses a procedure and assembly for drawing blood which involves the use of a portable instrument, as for example a specimen sampling tube tray, which has an onboard microprocessor which stores and uses information from the main hospital computer. An onboard label printer is also included in the instrument. The microprocessor is connected to and operates the printer. A bar code scanner is also mounted in the instrument and connected to the microprocessor. The scanner is used to scan a patient's wrist band at bedside. The scanned bar code tells the microprocessor who the patient is, and the microprocessor causes the printer to print a label at the bedside. The label will include the patient's printed accession number in bar code and alphanumeric form, and the patient's name, specimen testing instructions, and the time and date the specimen is drawn; the latter all being printed in human readable alphanumeric indicia.

Copending U.S. patent application Ser. No. 689,476 filed Apr. 23, 1991 by William E. Neeley et al also describes a procedure for drawing blood samples.

DISCLOSURE OF THE INVENTION

This invention relates to an improved procedure for drawing patient blood samples in capillary tubes and for labeling the drawn samples with labels that are printed at the patient's bedside, which labels include patient I.D.; time of sample taking; and specimen sample testing instructional information displayed thereon in machine readable and also in alphanumeric form. The procedure also involves the use of an improved carrier tube for holding the capillary tubes from each patient and to which carrier tube the aforesaid printed labels are applied.

The carrier tube will preferably be an appropriately sized glass tube that will have a closed bottom end, and a capped top end. The bottom end of the tube will preferably be provided with a resilient pad inside of the tube to cushion one end of capillary tubes placed in the tube. The cap will preferably have a cup-shape which telescopes over the sides of the tube. The interior of the cap will contain a layer of capillary tube closure putty which will be used to plug one end of each capillary tube containing a blood sample from the patient. The possibility of contaminating one patient's blood with another patient's blood from a putty source for all of the patient's blood is thus eliminated. The carrier tube will preferably contain an internal divider which will form single capillary tube cells in the tube so as to limit the chances of capillary tube breakage in the carrier tube which could otherwise occur by jostling of the tubes during handling.

The procedure preferably involves the use of a specialized specimen drawing tray of the type disclosed in the aforesaid copending U.S. Patent Applications. The tray is provided with a plurality of capillary specimen sampling tubes, and with a plurality of the aforesaid carrier tubes. The tray has an onboard microprocessor which stores collated patient ID and specimen testing information, and which receives patient ID information from an onboard scanner used to scan wristbands or patient bedside charts which display thereon a machine readable patient ID indicia, such as a bar code. The tray also has an onboard label printer which is driven by the microprocessor to print at bedside appropriate labels customized for the patient being scanned and sampled. The labels will display the appropriate patient ID; sampling time; and specimen test instructions in alphanumeric and machine readable indicia, and which labels are sized to be conveniently adhered to the carrier tubes. The drawer will print the label, affix it to the carrier tube, and draw the indicated number of specimens in capillary tubes which will be plugged with the putty carried in the carrier tube cap. The capillary tubes will then be placed in the cells in the labeled carrier tube, after which the carrier tube will be recapped and the next patient sampled. When the samples are brought to the lab, the lab personnel read the labels on each carrier tube and know immediately what tests are to be performed on the samples in the capillary tubes. They also know the time and date when the samples were drawn.

It is therefore an object of this invention to provide an improved procedure for drawing and labeling patient specimen samples in capillary tubes.

It is a further object of this invention to provide an improved procedure of the character described wherein filled capillary tubes from each patient are placed in a common carrier tube carrying a patient and specimen testing label.

It is an additional object of this invention to provide an improved procedure of the character described wherein the capillary tubes for each patient are plugged with a supply of closure putty which is not used to plug the capillary tubes of any other patient.

It is another object of this invention to provide an improved procedure of the character described wherein the supply of closure putty is carried by carrier tubes adapted to receive the capillary tubes of each patient, so that each carrier tube holds only capillary tubes and specimen samples from one patient.

These and other objects and advantages of the invention will become more readily apparent from the following detailed description of a preferred embodiment thereof when taken in conjunction with the accompanying drawings in which:

SPECIFIC EMBODIMENT

Figure 1:
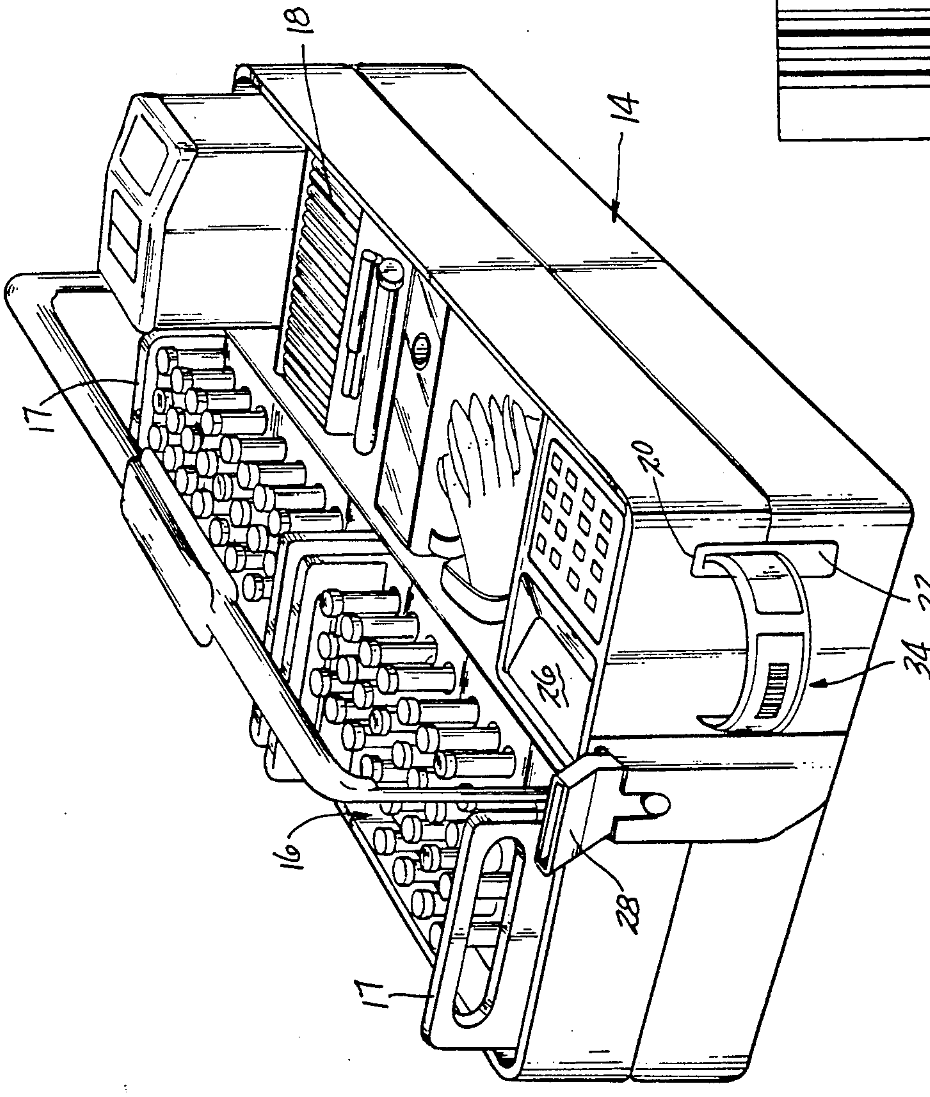
FIG. 1 is a perspective view of a blood specimen tube microprocessor-printer-scanner tray assembly for use in practicing this invention.

Referring now to FIG. 1, there is shown details of a blood sampling tray which has been adapted to operate in accordance with this invention. The tray 14 includes a portion 16 thereof which is adapted to receive a plurality of carrier tube racks 17 therein. A carrier tube label printer 20 is built into the tray 14. The printed carrier tube labels are ejected from the printer 20 via slot 22. It will be understood that the label printer 20 is preloaded with a roll of blank label strip 34 which is precoated with an adhesive and adhered to a non-bonding strip of material, such as waxed paper, or the like. Finished labels thus can be readily peeled from the waxed paper strip. The printer 20 is controlled by a microprocessor housed in the tray 14. The tray has a liquid crystal display 26 which may specify to the specimen drawer the number of capillary tubes, which are to be used to take specimens from the patient after the wrist band has been scanned.

A hand held bar code scanner 28 is operably connected to the tray microprocessor. The scanner 28 is preferably a laser or charge-coupled device scanner which is adapted to read the patient's ID bracelet which, due to the fact that it is worn on an irregular surface, i.e. one's wrist, is difficult for a conventional wand scanner to read.

The tray 14 also includes a well for receiving a plurality of capillary tubes 18 for use in drawing the blood samples.

Figure 2:
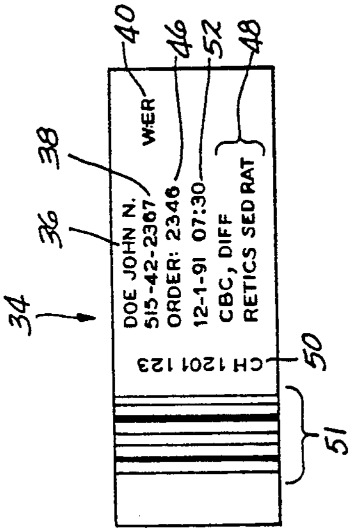
FIG. 2 is a plan view of a patient and specimen test instruction label for affixation to the carrier tube, which label is printed at bedside by the assembly of FIG. 1.

FIG. 2 shows a typical carrier tube label 34 produced by the printer 20 after the ID bracelet tag has been scanned. The label 34 displays the patient's name 36; ID number 38; the patient ward location 40; the patient order number 46; the tests to be performed 48 on the specimens; the patient test accession number in alphanumeric form 50 and in bar code form 51; and the time and date the specimens are drawn 52.

Figure 4:
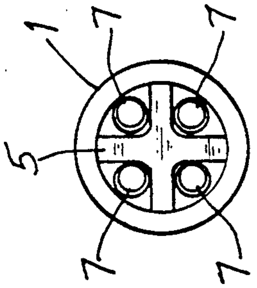
FIG. 4 is a top plan view of the tube of FIG. 3.
Figure 3:
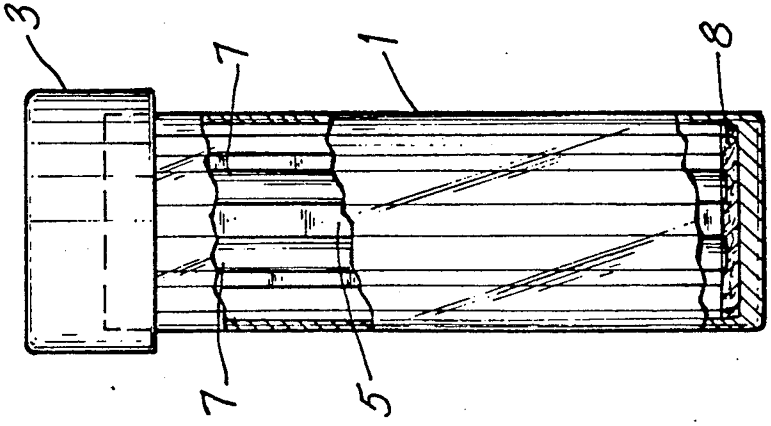
FIG. 3 is a side elevational view of a carrier tube which has a capillary tube confining insert disposed therein.

Referring to FIGS. 3 and 4, there is shown a capillary tube carrier tube 1 having a closure cap 3 positioned thereon and an internal divider 5 which subdivides the interior of the tube 1 into cells for receiving the capillary tubes 7 after the samples have been drawn. A pad 8 is positioned in the bottom of the tube 1 for cushioning the bottoms of the capillary tubes 7.

Figure 5:
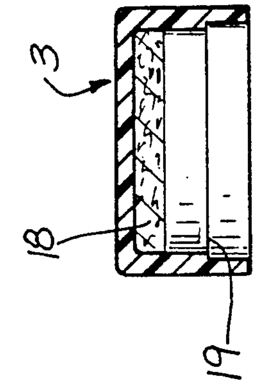
FIG. 5 is a cross sectional view of the carrier tube cap.

FIG. 5 shows the details of the cap 3. The cap 3 has a layer of closure putty 18 adhered to the inside of the top end thereof for use in plugging an end of capillary tubes placed therein after specimen samples have been drawn into the capillary tubes. A shoulder 19 is formed on the interior side wall of the cap 3 for engaging the top surface of the carrier tube 1 to limit the extent of telescoping of the cap 3 over the tube 1. This ensures that a gap will be preserved between the top ends of the capillary tubes 7 in the tube 1 and the putty layer 18 in the cap 3.

Figure 6:
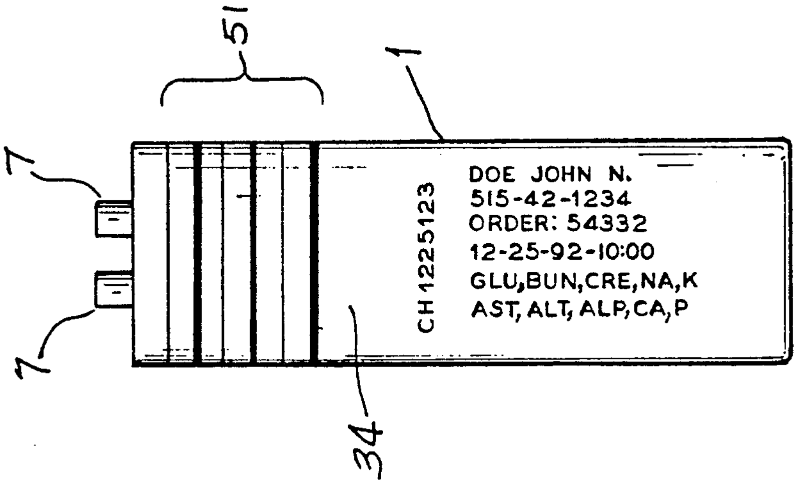
FIG. 6 is a view similar to FIG. 3, but showing a printed patient and specimen test instruction label affixed to the carrier tube.

FIG. 6 shows the tube 1 after the specimen label 34 has been printed and affixed to the tube 1 at bedside. The label 34 is properly positioned so as to place the bar coded patient accession number 51 in the proper place to be scanned by the automatic laboratory specimen testing equipment contained in modern hospitals. When the cap 3 has been removed from the tube 1, the capillary tubes 7 project above the top end of the carrier tube 1 so that the capillary tubes 7 can be easily manually removed from the carrier tube 1 in the laboratory.

It will be readily appreciated that this invention provides for safer, more accurate, specimen sampling of patients with customized labels as to form and information. The microprocessor label printer may be obtained from Pitney Bowes Corporation. The bracelet band tube scanners can be obtained from Opticon, Inc. While the invention had been described in connection with the taking of blood samples from hospital patients, it will be readily apparent that it can be used in connection with other specimen sampling of patients in other environs, such as clinics, physicians' offices, sanitariums, or the like. Likewise, the invention can be performed with other forms of machine readable means, such as a magnetically coded bracelet which can be scanned by a magnetic scanner. The invention allows the person who draws the samples to become markedly less involved in the reliability of the sampling, and allows blood samples in capillary tubes to be clearly labeled for the laboratory personnel. The possibility of contaminating one patient's blood sample with another patient's blood is markedly reduced.

Since many changes and variations of the disclosed embodiment of the invention may be made without departing from the inventive concept, it is not intended to limit the invention otherwise than as required by the appended claims.

What is claimed is:

1. A transfer tube assembly for transporting blood samples drawn in capillary tubes, said assembly including a transfer tube sized to contain a plurality of the capillary tubes, said transfer tube having a closed end and an open end; and a cap for closing the open end of said transfer tube, and said cap having a recess which contains sufficient putty to plug one end of each of the capillary tubes placed in the transfer tube whereby all capillary tubes in any one transfer tube will be plugged solely with putty from the cap associated with said one transfer tube.

2. The transfer tube assembly of claim 1 further comprising a cushioning pad disposed in the closed end of the transfer tube for engagement by one end of each capillary tube placed therein.

3. The transfer tube assembly of claim 1 further comprising divider means disposed in said transfer tube for forming individual capillary tube-receiving cells in the transfer tube.

4. The transfer tube assembly of claim 1 further comprising a label on said transfer tube displaying machine readable indicia specific to patients whose blood samples are contained in the transfer tube; and displaying alpha numeric blood specimen testing instructions specific to the blood samples contained in the transfer tube.

5. A method for drawing and identifying patient blood samples in capillary tubes, said method comprising the steps of:

a) providing a supply of capillary tubes at the locale of the patient; b) providing a supply of transfer tubes at the locale of the patient, said transfer tubes each being sized to receive and retain a plurality of the capillary tubes;

c) providing a supply of tube closures for closing said transfer tubes, each of said tube closures containing an onboard supply of capillary tube closure putty;

d) drawing a sample of blood from a patient into a capillary tube;

e) plugging and end of the filled capillary tube with putty from said onboard putty supply in one of said tube closures;

f) placing the filled, plugged capillary tube in one of said transfer tubes; and g) closing said one of said transfer tubes with said one of said tube closures after a desired number of filled, plugged capillary tubes containing blood from the same patient are placed in said one of said transfer tubes.

6. The method of claim 5 comprising the further steps of printing a specimen label at the patient's locale said label identifying the patient, and the tests to be performed on the blood samples; and affixing said label to the transfer tube.

7. A capillary tube carrier assembly for transporting specimen samples drawn in capillary tubes, said assembly including a transfer tube having a closed end and an open end; a cap for closing the open end of said transfer tube, said cap having a recess which contains sufficient putty to plug one end of each of the capillary tubes placed in the transfer tube whereby all capillary tubes in said transfer tube will be plugged solely with putty from the cap associated with said transfer tube; divider means disposed in said transfer tube for forming individual capillary tube-receiving cells in said transfer tube; and at least one capillary tube disposed in one of said tube-receiving cells.

8. The carrier assembly of claim 7 further comprising a cushioning pad disposed in the closed end of said transfer tube for engagement by one end of each capillary tube polaced therein.

9. The carrier assembly of claim 7, wherein said capillary tube extends past said open end of said transfer tube so as to be easily removable manually from said transfer tube.

10. The carrier assembly of claim 9 wherein said cap includes an internal shoulder formed thereon for engagement with the open end of said transfer tube, said shoulder being operable to ensure that capillary tubes disposed in said transfer tube remain free from contact with said putty in said cap recess.

* * * * *